United States Patent [19]

Harold

[11] Patent Number: 4,857,333
[45] Date of Patent: Aug. 15, 1989

[54] FOOD PRODUCT FOR ADMINISTERING MEDICATION TO ANIMALS

[76] Inventor: Robert G. Harold, 3724 Aster Ct., Philadelphia, Pa. 19136

[21] Appl. No.: 192,962

[22] Filed: May 12, 1988

[51] Int. Cl.⁴ .............................................. A23K 1/17
[52] U.S. Cl. .................... 424/442; 424/405; 424/440; 426/94; 426/104; 426/138; 426/144; D1/106; D1/199
[58] Field of Search .................. 426/75, 134, 442, 89, 426/94, 282, 283, 279, 280, 805, 104, 138, 144; 424/440, 442, 405; D1/106, 199

[56] References Cited

U.S. PATENT DOCUMENTS

| | | | |
|---|---|---|---|
| 153,421 | 7/1874 | Butts | 424/439 |
| D. 254,337 | 3/1980 | Miller | D1/106 |
| D. 291,740 | 9/1987 | Spiel | D1/106 |
| 3,005,753 | 10/1961 | Vierling | 424/442 |
| 3,840,678 | 6/1970 | Price | 426/104 |
| 4,163,065 | 7/1979 | Cilek | 426/104 |
| 4,551,329 | 11/1985 | Harris et al. | 424/22 |

FOREIGN PATENT DOCUMENTS

0004921 of 1877 United Kingdom .............. 424/442

OTHER PUBLICATIONS

Better Homes & Gardens, p. 204, Oct. 1979, Ralston Purina Co.

Primary Examiner—Ellis P. Robinson
Assistant Examiner—Archene A. Turner
Attorney, Agent, or Firm—Steele, Gould & Fried

[57] ABSTRACT

An animal food product for administering medication to animals is a formed, chewable food treat with at least one pre-formed pocket therein opening to an outer surface of the treat and sized to retain a medicant therein.

6 Claims, 1 Drawing Sheet

FOOD PRODUCT FOR ADMINISTERING MEDICATION TO ANIMALS

BACKGROUND OF THE INVENTION

1. Field of the Invention

This invention relates to a food product for animals and more particularly, to a food product which includes a pocket in which medication may be concealed.

2. Description of the Prior Art

Most pet owners have experienced difficulty administering oral medication to their pets, particularly dogs. In order to get a pill into a dog, the dog's mouth must be held open while a pill is inserted into the back of the throat. Then the dog's mouth must be held closed while swallowing is encouraged. It often takes two people to complete this maneuver and many owners are injured by their pets, and many pets are injured by their owners, while administering pills. Pet owners have tried to conceal pills and mask the taste of pills by wrapping them in cheese or lunch meat, but the pill often escapes its wrappings.

Solutions intended for humans do not readily adapt to animals. For example, U.S. 153,329 to Butts discloses the use of a fig as an envelope for administering medicine to children, an uneconomical, and possibly non-nutritional, solution for pets. U.S. 4,551,329 to Harris et al discloses a lollipop with medication enclosed in "ears" formed by extensions of the lollipop stick. An animal can not be safely treated with a lollipop.

Some medications may be available in a form which is edible and palatable to the pet, such as disclosed by Vierling in U.S. 3,005,753. However, most pets will learn to distinguish that particular food item from other food products, and the problem still remains of administering other medications not adaptable to Vierling's solution.

It is desirable to administer medication in a readily acceptable form, and in particular, one which the animal has come to accept without medication. It is also desirable to have a means of administering medication which may be used for a variety of pills, as treatment requires.

SUMMARY OF THE DISCLOSURE

The aforementioned prior art problems are obviated by the animal food product of this invention. A food treat for animals (such as a bone-shaped rigid dry dog food treat or a soft-formed rounded dog treat) includes a pre-formed pocket opening on the outer surface of the treat. The pocket is sized to conceal and retain a pill for treatment or prevention of animal diseases. It is preferable that the pocket be tapered toward the interior of the treat to ensure better retention of the pill. If the treat is regularly given to the pet without a pill, the pet will readily accept the treat when a pill is inserted.

It is, therefore, an object of this invention to provide a simple and safe means for administering medication to animal pets.

It is another object of this invention to provide an animal food product which conceals medication in a pre-formed empty pocket.

It is still another object of this invention to provide an animal food product which may be fed to an animal with or without medication in its pocket.

It is yet a further object of this invention to provide means to medicate an animal which is available in either a dry rigidly formed treat or in a semi-rigid moist food product.

These and other objects will be more readily ascertainable to one skilled in the art from a consideration of the following Figures, description and exemplary embodiments, with the understanding that the drawings are illustrative only and that changes may be made in the specific construction illustrated and described within the scope of the appended claims.

BRIEF DESCRIPTION OF THE DRAWING(S)

DETAILED DESCRIPTION OF THE PREFERRED EMBODIMENT(S)

Figure 1:
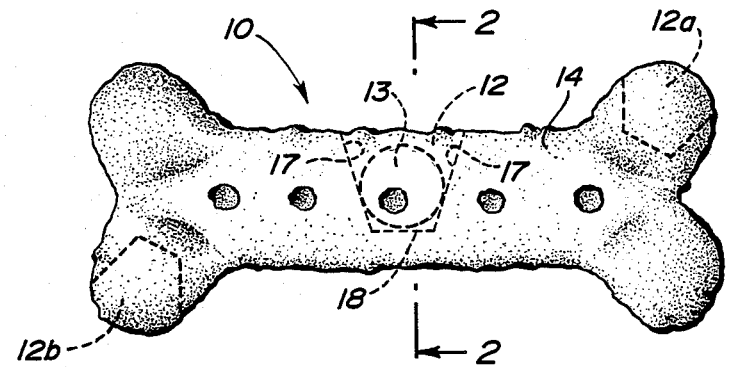
FIG. 1 is a top elevational view of a bone-shaped rigid dog food product including a medication pocket with a pill enclosed.

Referring now to the drawings, it should be understood that although the drawings illustrate and are described as showing conventional dog treat food products, food products for other animals, such as horses, cats, rabbits, hamsters and the like pets may also be provided with a pill pocket and still be within the scope of this invention. The foods and fillers from which the food product according to this invention will be made will vary among the various animals and breeds of animals being treated. The foods and fillers will correspond to those from which conventional food products are already made.

Figure 2:
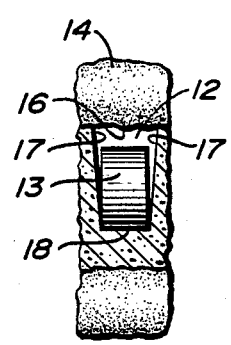
FIG. 2 is a cross sectional view taken on line 2—2 of FIG. 1.
Figure 3:
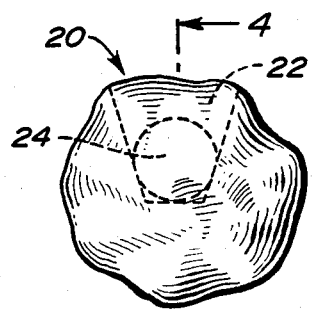
FIG. 3 is a top elevational view of a rounded, semi-rigid food product including a medication pocket with a pill enclosed.
Figure 5:
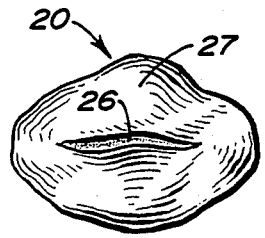
FIG. 5 is a side view of the food product of FIG. 3 showing the slot entrance to the pocket.
Figure 4:
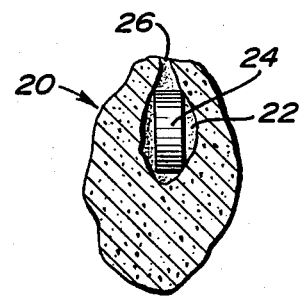
FIG. 4 is a cross sectional view taken on line 4—4 of FIG. 3.

Now referring to FIGS. 1 and 2, a rigid dog food product is shown as bone-shaped treat 10. Treat 10 has a plurality of pill pockets, pockets 12, 12a and 12b. It is preferred that one pocket 12 be provided, but it may be useful to have a plurality of pockets for use when more than one medication is prescribed for the animal at one time.

Pocket 12, which has sides 17 and end 18, opens at mouth 16 formed in treat surface 14. It is preferred that pill pocket 12 is tapered, sides 17 converging so that end 18 is shorter than open mouth 16. Thus, when pill 13 (or other medicant) is inserted through mouth 16, it may be urged into pocket 12 until it is frictionally retained therein by sides 17.

The size of food product treat 10 will depend upon the animal being treated. A large animal will consume a small bone treat 10 at once, taking the whole treat into its mouth. A smaller animal will take bites off the treat. In that case, it may be preferred to have the pill concealed in a pocket (12a or 12b) at one end of the treat rather than in the center (pocket 12). If food product treat 10 is made as a hard and dry dog food treat, for example, as is otherwise well known in the art, it will readily break apart when a dog is chewing it. If the whole treat is consumed at once, the pill and the broken treat pieces will be swallowed together. Again, if this treat is the type normally fed to the pet, the pet will take the medicated treat without urging and the medication will be administered without trouble.

Figure 6:
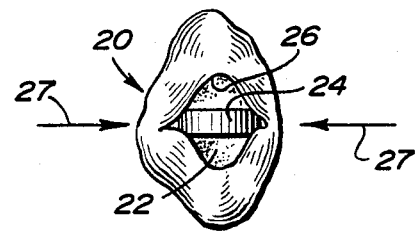
FIG. 6 shows the food product of FIG. 3 deformed and a pill inserted through the slot.

Now referring to FIGS. 3, 4, 5 and 6, an alternative embodiment of food product treat 20 includes pill pocket 22. Food product 20 is a soft, moist food product which may be provided in a variety of shapes. The rounded treat herein illustrated is illustrative only. Food product 20 is deformable when manually squeezed or pressed. Slot 26 is seen in surface 27 of treat 20. Slot 26 provides entrance into pocket 22 which is preformed in treat 20. Because treat 20 is deformable, when it is pressed in the direction of arrows 27, slot 26 deforms and opens to allow insertion of pill 24 into pocket 22, as illustrated in FIG. 6. Pocket 22 is sized so that it will closely retain pill 24, or other rigid or non-rigid medication. Because slot 26 recloses after pill 24 is in pocket 22, the medication is securely held inside treat 20. It is clearly an advantage over the conventional "slice of cheese method" to use treat 20 to administer medication to a pet because the pill or other medication will not escape from the treat.

As with the rigid treat 10, the size of treat 20 will depend upon the animal being treated. Although soft treats are generally of a smaller size than hard food treat, they may be adapted as necessary for the size of conventional animal pills. It is to be expected that the soft treats will be taken into the dog's mouth as one piece. As the dog chews the treat, the pill will be consumed simultaneously.

There are several variations which can be practiced in the scope of this invention. The treat may be either rigid or semi-rigid, as long as it includes a pocket for retaining medication. The treat may be provided in a variety of shapes and sizes as long as the treats are chewable and include pill pockets.

There are many advantages to the food treat for administering medication of this invention. Chiefly, by administering medication in a food treat, the pet owner does not need to force the medication down the pet's throat. Not only is this an easier way to administer medicine, but it safer and more pleasant for the owner and the pet.

Having now illustrated and described the invention, it is not intended that such description limit this invention, but rather that this ivention be limited only by reasonable interpretation of the appended Claims.

What is claimed is:

1. An animal food product for administering medication to animals, comprising:
   a formed, chewable food treat having at least one pre-formed empty pocket therein opening onto an outer surface of said treat, the pre-formed pocket being dimensioned to engage a medicant when placed therein, the medicant being retained within the pocket, whereby an animal may be habituated to the food product when unmedicated, and when necessary, the medicant can be concealed therein.

2. An animal food product for administering medication to animals, comprising:
   a formed, chewable food treat having at least one pre-formed pocket therein, opening onto an outer surface of said treat and sized to conceal and retain a medicant therein, the pocket being tapered to frictionally engage the medicant, whereby an animal may be habituated to an unmedicated food product which, when necessary, can have a medicant concealed therein.

3. The animal food product according to claim 1 wherein said food treat is rigid and said food treat is dry.

4. An animal food product for administering medication to animals, comprising:
   a formed, chewable food treat having at least one pre-formed empty pocket therein opening onto an outer surface of said treat, the pocket being sized to encompass a medicant to be placed therein, the food treat being semi-rigid and moist, whereby an animal may be habituated to the product as unmedicated, and which when necessary, can have the medicant concealed therein, the pocket being deformed to close after placing the medicant therein.

5. The animal food product according to claim 1 wherein said food treat is bone-shaped and includes a plurality of said pockets.

6. The animal food product according to claim 1 wherein said food treat is sized so that an entire treat may be taken into an animal's mouth at once.

* * * * *